US008753832B2

(12) United States Patent
Umegae et al.

(10) Patent No.: US 8,753,832 B2
(45) Date of Patent: Jun. 17, 2014

(54) METHOD OF ASSAYING 1,5 ANHYDROGLUCITOL BY USING WHOLE BLOOD AND MEASUREMENT KIT

(75) Inventors: Yoshihiko Umegae, Takasaki (JP); Reiko Machida, Takasaki (JP); Yayoi Irie, Takasaki (JP); Toshio Tanabe, Takasaki (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 838 days.

(21) Appl. No.: 11/921,917

(22) PCT Filed: Jun. 12, 2006

(86) PCT No.: PCT/JP2006/311752
§ 371 (c)(1),
(2), (4) Date: Dec. 10, 2007

(87) PCT Pub. No.: WO2006/134870
PCT Pub. Date: Dec. 21, 2006

(65) Prior Publication Data
US 2010/0075352 A1    Mar. 25, 2010

(30) Foreign Application Priority Data
Jun. 13, 2005    (JP) ................................ 2005-172264

(51) Int. Cl.
*C12Q 1/54* (2006.01)

(52) U.S. Cl.
USPC .............................................. 435/14; 435/25

(58) Field of Classification Search
None
See application file for complete search history.

(56) References Cited

U.S. PATENT DOCUMENTS

| | | | |
|---|---|---|---|
| 4,810,640 A | 3/1989 | Nakamura et al. | |
| 4,916,069 A | 4/1990 | Fujiwara et al. | |
| 4,994,377 A | 2/1991 | Nakamura et al. | |
| 5,374,546 A | 12/1994 | Nagel et al. | |
| 5,407,806 A | 4/1995 | Yabuuchi et al. | |
| 5,426,033 A * | 6/1995 | Kojima et al. | 435/14 |
| 5,821,073 A | 10/1998 | Lee | 435/7.92 |
| 5,871,949 A | 2/1999 | Ebinuma et al. | |
| 6,268,166 B1 | 7/2001 | Kojima et al. | |
| 6,448,029 B1 | 9/2002 | Tazoe et al. | |
| 6,541,215 B1 | 4/2003 | Ebinuma et al. | |
| 6,764,581 B1 | 7/2004 | Forrow et al. | |
| 2002/0027072 A1 | 3/2002 | Cui et al. | 204/403.1 |
| 2004/0053349 A1 | 3/2004 | Citri | |
| 2010/0062469 A1 | 3/2010 | Umegae et al. | |
| 2010/0075352 A1 | 3/2010 | Umegae et al. | |
| 2011/0031118 A1 | 2/2011 | Machida et al. | |
| 2011/0165608 A1 | 7/2011 | Machida et al. | |

FOREIGN PATENT DOCUMENTS

| | | |
|---|---|---|
| CN | 1257128 A | 6/2000 |
| EP | 0 159 727 | 10/1985 |
| EP | 0 436 897 | 7/1991 |
| JP | 62-79780 A | 4/1987 |
| JP | 63-22185 A | 1/1988 |
| JP | 63-185397 A | 7/1988 |
| JP | 2-268679 A | 11/1990 |
| JP | 3-27299 | 2/1991 |
| JP | 4-212060 | 8/1992 |
| JP | 5-76397 | 3/1993 |
| JP | 5-223773 A | 8/1993 |
| JP | 7-67697 A | 3/1995 |
| JP | 7-36756 B2 | 4/1995 |
| JP | 8-70893 A | 3/1996 |
| JP | 8-298996 A | 11/1996 |
| JP | 10-10125 | 1/1998 |
| JP | 10-62402 A | 3/1998 |
| JP | 10-179140 A | 7/1998 |
| JP | 10-191998 A | 7/1998 |
| JP | 11-18760 A | 1/1999 |
| JP | 2872983 B2 | 1/1999 |
| JP | 2983015 B2 | 9/1999 |
| JP | 2000-135079 A | 5/2000 |
| JP | 2000-175698 A | 6/2000 |
| JP | 2001-78797 A | 3/2001 |
| JP | 3170320 B2 | 3/2001 |
| JP | 2001-116756 A | 4/2001 |
| JP | 2001-133430 A | 5/2001 |
| JP | 2001-190299 A | 7/2001 |
| JP | 2001-197900 A | 7/2001 |
| JP | 3217180 B2 | 8/2001 |

(Continued)

OTHER PUBLICATIONS

Tanaka Y. et al. Microvolume Blood-Sampling Device with Low Hemolysis and High Consistent Yield of Serum Components, Clinical Chemistry (2001), vol. 47(10): pp. 1829-1835.*

(Continued)

*Primary Examiner* — Satyendra Singh
(74) *Attorney, Agent, or Firm* — Nields, Lemack & Frame, LLC

(57) ABSTRACT

In quickly assaying a blood component interfered by glucose and/or its derivative on the bedside or in a clinic or in assaying the same by a patient in his/her own home, there has been required an assay method wherein the whole blood can be used as a sample as such without resorting to a centrifuge or the like. A method of assaying a blood component to be used for assaying a blood component interfered by glucose and/or its derivative, characterized by comprising bringing the whole blood into contact with a substance capable of converting glucose and/or its derivative into another substance not interfering the assay and, simultaneously or subsequently, separating blood cells; a device to be used in the assay method; and a kit containing this device.

5 Claims, 1 Drawing Sheet

(56) References Cited

FOREIGN PATENT DOCUMENTS

| JP | 2002-90331 | 3/2002 |
|---|---|---|
| JP | 2002-514744 A | 5/2002 |
| JP | 2003-83958 | 3/2003 |
| JP | 5-304997 A | 11/2003 |
| JP | 2005-523443 A | 8/2005 |
| JP | 3713049 B2 | 8/2005 |
| JP | 2006-275819 A | 10/2006 |
| WO | 96/25514 A1 | 8/1996 |
| WO | 02/33407 | 4/2002 |
| WO | 2006/134870 A1 | 12/2006 |

OTHER PUBLICATIONS

Clinical Chemistry, vol. 40, No. 11, 1994 pp. 2013-2016; Yukihito Fukumura etal.; "Fully Enzymatic Method for determining 1,5-Anhydro-D-glucitol in Serum"; XP-002478498
European communication dated May 30, 2008.
Biomedical Chromatography, vol. 7, (1993) pp. 41-44, "Determination of 1,5-Anhydroglucitol in Urine by High Performance Liquid Chromatography and an Enzyme Sensor", by Tajima, et al.
Clinica Chimica Acta 350 (2004), pp. 201-209, "Evaluation of an assay for serum 1,5-anhydroglucitol (GlycoMark) and determination of reference intervals on the Hitachi 917 analyzer", by Nowatzke, et al.
Denki Kagaku, V. 63, No. 10 (1995), with partial English translation, pp. 906-911.
European Communication dated Dec. 4, 2009 in co-pending foreign application PCT/JP2007/074047/co-pending U.S. Appl No. 12/448,129
International Search Report dated Mar. 25, 2008 in co-pending foreign application PCT/JP2007/074047/co-pending U.S. Appl. No. 12/448,129.
Chinese Communication, with English translation, dated May 31, 2011 in corresponding foreign patent application No. CN 200680028932.0 (document serial No. 2011052600534800).
Office Action mailed Dec. 28, 2011 in co-pending U.S. Appl. No. 12/448,120.
Diabetes Care, vol. 27, No. 8, Aug. 2004, pp. 1859-1865, "Circulaing 1,5-Anhydroglucitol Levels in Adult Patients With Diabetes Reflect Longitudinal Changes of Glycemia", McGill, et al.
Office Action (Restriction) dated Jul. 14, 2011 in co-pending U.S. Appl. No. 12/448,120.
Office Action dated Sep. 2, 2011 in co-pending U.S. Appl. No. 12/448,120.
Chinese Communication, with English translation, dated Dec. 28, 2012 in co-pending Chinese Patent Application No. 200780046209.X.
Japanese Communication mailed Jul. 13, 2012 in co-pending Japanese Patent Application No. 2008-549361.
Final Rejection mailed May 3, 2012 in co-pending U.S. Appl. No. 12/448,120.
Merck Manual Home Edition, Section: Hormonal and Metabolic Disorders, Chapter: "Diabetes Mellitus", 12 pages, last full review/revision in Jun. 2008 by Preeti Kishore, MD, accessed Aug. 19, 2012 @ http://www.merckmanuals.com/home/print/hormonal_and_metabolic_disorders/diabetes_mellitus.
Kimball's Biology Pages (online biology textbook), "Transport Across Cell Membranes", 10 pages, Feb. 5, 2011, by John W. Kimball, accessed Aug. 19, 2012 @ http://users.rcn.com/jkimball.ma.ultranet/BiologyPages/D/diffusion.html.
Biochimica et Biophysica Acta, vol. 255, 1972, pp. 126-132, "Kinetic Parameters of Glucose Efflux From Human Red Blood Cells Under Zero-Trans Conditions", Karlish, et al.
Diabetes Care, vol. 4, No. 5, Sep.-Oct. 1981, pp. 551-555, "Glycosylated Hemoglobin in Relation to Rapid Fluctuations in Blood Glucose in Children with Insulin-dependent Diabetes: A Comparison of Methods With and Without Prior Dialysis", Ditzel, et al.
Clinical Chemistry, vol. 35, No. 2, 1989, pp. 315-317, "Effectiveness of Sodium Fluoride as a Preservative of Glucose in Blood", Chan, et al.
Office Action mailed Nov. 8, 2012 in co-pending U.S. Appl. No. 12/448,120.
Notice of Allowance mailed Apr. 1, 2013 in co-pending U.S. Appl. No. 12/448,120.

\* cited by examiner

POSITION AT WHICH SPECIMEN IS PLACED

DEVICE

POSITION AT WHICH SPECIMEN IS PLACED

DEVICE

METHOD OF ASSAYING 1,5 ANHYDROGLUCITOL BY USING WHOLE BLOOD AND MEASUREMENT KIT

This application is a National Stage U.S. Application filed under Rule 371 based upon PCT/JP2006/311752 filed Jun. 12, 2006.

TECHNICAL FIELD

The present invention relates to a method for measuring a blood component that is subject to interference caused by glucose and/or a derivative thereof, characterized in that whole blood is used, whole blood and a substance converting glucose and/or a derivative thereof to a substance that does not interfere with the measurement are brought into contact with each other, and blood cells are simultaneously or subsequently isolated, a device used for the measurement, and a kit including the device.

BACKGROUND ART

Measurement of electrolytes, proteins, nonprotein nitrogen compounds, sugars, lipids, enzymes, and the like in blood is called clinical chemistry examination, which is an important test for diagnosis, treatment, and prevention of a disease. Quite a many substances other than target substances to be measured exist in blood used as a test sample and often interfere with measurement of a target substance. Therefore, techniques are adopted in which a specimen is treated with an agent for avoiding the interference before measuring the target substance. At this time, collected whole blood is usually centrifuged or the like to obtain plasma or serum beforehand. This is because, when blood component analysis using whole blood as a sample that requires elimination or conversion of components interfering with the measurement is performed, cell components such as blood cells may affect the measurement, isolation of blood cells may be difficult due to hemolysis, hemoglobin having a peroxidase activity, which abundantly exists in blood cells, may interfere with the measurement, and the like.

In recent years, the number of diabetic patients has been increasing as the diet has become richer. To prevent complications in diabetic patients, blood sugar levels need to be maintained at the levels close to those of healthy individuals, and apparatuses for self-measurement of blood sugar levels are widely used so that patients can monitor the blood sugar levels themselves at home. However, since blood sugar levels vary depending on the meal, and the measurement has to be done frequently, patients suffer heavy burdens. It is also difficult for patients to interpret measured values due to lack of knowledge.

Meanwhile, 1,5-anhydroglucitol is an excellent marker for checking a blood sugar control condition in diabetic patients over the past one week without being affected by meals, and development of a self-measurement kit using 1,5-anhydroglucitol, which can accurately check a blood sugar control condition at home by once-weekly measurement alone, will be of a great advantage for patients. Furthermore, it would also be useful in mass screening. However, since the concentration of 1,5-anhydroglucitol in blood is extremely low compared with the blood sugar level, and blood sugar, i.e., glucose interferes with measurement of 1,5-anhydroglucitol, development of self-measurement kits including those using a trace amount of whole blood as a sample as it is has not been realized.

Furthermore, glucose exists at a high concentration in the intracellular fluid in a blood cell and is balanced with glucose in the extracellular fluid across the cell membrane. If glucose in the extracellular fluid is converted to a substance that does not interfere with measurement, glucose in the intracellular fluid in the blood cell is released through the cell membrane and interferes with the measurement.

Examples of the blood component analysis requiring elimination or conversion of components that interfere with measurement include those described in the following publications. In Patent Document 1, blood cells are isolated from whole blood, and then ascorbic acid, a component interfering with measurement, is eliminated by ascorbic acid oxidase to measure creatinine.

In Patent Documents 2, 3, and 4, not whole blood but serum is used as a specimen to measure sorbitol in Patent Document 2, mannose in Patent Document 3, and myoinositol in Patent Document 4. In any case, glucose, a component interfering with measurement, is eliminated or converted in pretreatment.

When 1,5-anhydroglucitol is to be measured, not whole blood but serum is used as a specimen as described in Patent Documents 5, 6, 7, 8, and the like. Glucose is oxidized by glucose oxidase or also phosphorylated by hexokinase or glucokinase in Patent Document 5, is oxidized by glucose oxidase or glucose dehydrogenase in Patent Document 6, and is converted to fructose-1,6-diphosphate by hexokinase, phosphohexose isomerase, and 6-phosphofructokinase or glucose isomerase, fructokinase, and 6-phosphofructokinase in Patent Documents 7 and 8, and then 1,5-anhydroglucitol is measured. It is noted that glucose is converted to glucono-1, 5-lactone, glucose-6-phosphate, gluconic acid, fructose-6-phosphate, fructose, or the like in these publications.

In these measurements of blood components, whole blood is not directly used as a sample, and use of a centrifuge and a large amount of blood are required to isolate blood cells, with many process steps of treatment.

Furthermore, a device to which a member is connected by external manipulation is described in Patent Document 1.
Patent Document 1: JP-B-07-36756
Patent Document 2: JP-A-08-298996
Patent Document 3: JP-A-2001-197900
Patent Document 4: JP-A-2001-190299
Patent Document 5: Japanese Patent No. 2983015
Patent Document 6: JP-A-2001-78797
Patent Document 7: Japanese Patent No. 3170320
Patent Document 8: Japanese Patent No. 3217180

DISCLOSURE OF THE INVENTION

Problems to be Solved by the Invention

Recently, however, rapid measurement at bedside or in a clinic called Point of Care Testing and measurement by patients themselves at home have been increasingly implemented. Since use of a centrifuge or the like is difficult in such cases, a measurement method using whole blood as it is as a test sample is desired. In particular, in the measurement by patients themselves at home, a trace amount, such as not more than several tens µL, of blood collected using a lancet device is used as a sample. Therefore, measurement methods using a centrifuge to obtain serum cannot be employed.

Means for Solving the Problems

The present inventors conducted various researches in order to solve the foregoing problems. As a result, they found a method for measuring a blood component that is subject to interference caused by glucose and/or a derivative thereof, in which whole blood is used as a sample and blood cells are isolated without using a centrifuge or the like, and accomplished the present invention.

That is, the present invention relates to the followings.

(1) A method for measuring a blood component that is subject to interference caused by glucose and/or a derivative thereof, characterized in that whole blood and a substance converting glucose and/or a derivative thereof to a substance that does not interfere with the measurement are brought into contact with each other, and blood cells are simultaneously or subsequently isolated.

(2) The method for measuring a blood component according to the above (1), wherein the amount of whole blood is not more than 20 μL.

(3) The method for measuring a blood component according to the above (1) or (2), characterized in that blood cells are isolated by using a filtration material for blood cell separation.

(4) The method for measuring a blood component according to the above (3), characterized in that the filtration material for blood cell separation is a glass fiber filter paper, a cellulose filter paper, a microporous material, a polymer material, or a member that is a combination thereof.

(5) The method for measuring a blood component according to any one of the above (1) to (4), wherein the substance converting glucose and/or a derivative thereof to a substance that does not interfere with the measurement is a substance used for enzymatic oxidation or enzymatic phosphorylation of glucose.

(6) The method for measuring a blood component according to any one of the above (1) to (5), characterized in that the substance converting glucose and/or a derivative thereof contains one or more compounds selected from the compound group consisting of phosphoenolpyruvic acid, α-ketoglutaric acid, oxaloacetic acid, acetylphosphoric acid, pyruvic acid, 3-phosphoglyceric acid, creatine phosphate, adenosine-5'-diphosphate, adenosine-5'-triphosphate, oxidized or reduced nicotinamide adenine dinucleotide, and oxidized or reduced nicotinamide adenine dinucleotide phosphoric acid.

(7) The method for measuring a blood component according to any one of (1) to (6), wherein the blood component is 1,5-anhydroglucitol.

(8) A device used in the method for measuring a blood component according to any one of (1) to (7), characterized by comprising a blood cell isolation part and a detection part.

(9) The device according to (8), wherein the blood cell isolation part and the detection part are out of contact before measurement, and these parts are brought into contact with each other to perform detection and quantification.

(10) The device according to (8), wherein the detection part is a detection part using an electrode coated with a reagent.

(11) A measurement kit comprising the device according to any one of (8) to (10) and a lancet device for collecting blood, wherein the blood component is 1,5-anhydroglucitol.

Effects of the Invention

In a method for measuring a blood component that is subject to interference caused by glucose and/or a derivative thereof, measurement can be performed without being affected by cellular components such as blood cells in whole blood or causing hemolysis, which interferes with measurement, by bringing whole blood and a substance converting glucose and/or a derivative thereof to a substance that does not interfere with the measurement into contact and simultaneously or subsequently isolating blood cells. Furthermore, since a centrifuge or the like is not used, measurement is made convenient, and the structure of a measurement device or a measurement kit can be simplified, thus lowering costs.

BEST MODE FOR CARRYING OUT THE INVENTION

Hereafter, the present invention will be explained in detail.

The present invention is a method for measuring a blood component that is subject to interference caused by glucose and/or a derivative thereof, characterized in that whole blood and a substance converting glucose and/or a derivative thereof to a substance that does not interfere with the measurement are brought into contact with each other, and blood cells are simultaneously or subsequently isolated.

Whole blood used in the present invention is blood in a state as collected from which erythrocytes are not isolated, and may contain an anticoagulant, a glycolytic inhibitor, and the like contained in a blood-collecting vessel for blood collection, such as heparin, sodium fluoride, and monoiodoacetic acid. When stored blood is used, blood is preferably collected by a blood-collecting vessel containing sodium fluoride and heparin.

Furthermore, the whole blood of the present invention includes blood collected by a lancet device or the like used for self-measurement of blood sugar levels without a blood-collecting vessel or the like.

Blood collection sites are not particularly limited and include a tip of a finger as well as the outside of the forearm, the abdominal wall or the outside of the upper arm.

According to the measurement method of the present invention, a blood component can be measured using even a small amount of whole blood. For example, 3 to 50 μL, preferably, 3 to 20 μL is sufficient.

Examples of the blood component in whole blood to be measured by the measurement method of present invention include 1,5-anhydroglucitol, sorbitol, mannose, or myoinositol, but are not limited to such sugars or sugar alcohols so long as they are to be measured in measurement of whole blood that may be interfered by glucose and/or a derivative thereof.

The substance converting glucose and/or a derivative thereof to a substance that does not interfere with the measurement in the present invention is not particularly limited so long as it does not affect measurement of a target blood component.

Examples thereof include the above-mentioned substances converting glucose and/or a derivative thereof to a substance that does not interfere with the measurement described in Patent Documents 2 to 8, preferably substances used for enzymatic oxidation or enzymatic phosphorylation of glucose. For example, substances described in the following explanation of enzymatic oxidation or enzymatic phosphorylation of glucose may be used. The substances converting glucose and/or a derivative thereof to a substance that does not interfere with the measurement in the present invention are substances that contract or agglutinate blood cells by actions such as osmolarity, reduce hematocrit (viscosity of blood) and thus promote isolation of blood cells from whole blood, so that a larger amount of plasma and serum can be obtained from a smaller amount of whole blood. Examples thereof include substances containing one or more compounds selected from the compound group consisting of phosphoenolpyruvic acid, α-ketoglutaric acid, oxaloacetic acid, acetylphosphoric acid, pyruvic acid, 3-phosphoglyceric acid, creatine phosphate, adenosine-5'-diphosphate (ADP), adenosine-5'-triphosphate (ATP), oxidized or reduced nicotinamide adenine dinucleotide (NAD(H)), and oxidized or reduced nicotinamide adenine dinucleotide phosphoric acid (NADP(H)).

Examples of the above-mentioned enzymatic oxidation or enzymatic phosphorylation of glucose include a method comprising oxidizing glucose by glucose oxidase, a method comprising oxidizing glucose by glucose dehydrogenase in the presence of a coenzyme nicotinamide adenine dinucleotide or nicotinamide adenine dinucleotide phosphoric acid, a method comprising phosphorylating glucose by hexokinase or glucokinase, and oxidizing the generated glucose-6-phosphate by glucose-6-phosphate dehydrogenase in the presence of a coenzyme $NAD^+$ or $NADP^+$, a method comprising allowing hexokinase, phosphohexose isomerase, and 6-phosphofructokinase to act in the presence of adenosine-5'-diphosphate or adenosine-5'-triphosphate to convert glucose to fructose-1,6-diphosphate, and a method comprising allowing glucose isomerase, fructokinase, and 6-phosphofructokinase in the presence of a nucleoside diphosphate (NDP) or a nucleoside triphosphate (NTP) to act to convert glucose to fructose-1,6-diphosphate.

Enzymes used for the above-mentioned conversions are not particularly limited so long as they are classified as glucose oxidase (EC1.1.3.4), glucose dehydrogenase (EC1.1.1.47, EC1.1.1.118, EC1.1.1.119, EC1.1.99.10), hexokinase (EC2.7.1.1), glucokinase (EC2.7.1.2); glucose-6-phosphate ketol-isomerase (EC5.3.1.9) as phosphohexose isomerases, glucose isomerase (EC5.3.1.18), and fructokinase (EC2.7.1.4); and phosphohexokinase (EC2.7.1.11) as 6-phosphofructokinase according to the IUPAC-IUB nomenclature, and those commercially available can also be used.

Furthermore, in the method comprising oxidizing glucose by glucose oxidase or glucose dehydrogenase, gluconolactonase (EC3.1.1.17) can also be used to convert the generated glucono-1,5-lactone completely to gluconic acid, and mutarotase (EC5.1.3.3) may be used in combination, if necessary. There is no problem in the use of an NDP-dependent hexokinase, such as ADP-dependent hexokinase, in particular, as a hexokinase.

In the measurement method of the present invention, preferred examples of enzymatic oxidation or phosphorylation of glucose include a method comprising phosphorylating glucose by hexokinase, and a particularly preferred example thereof is an enzyme cycling method using hexokinase in the presence of magnesium ion, ATP, phosphoenolpyruvic acid, and pyruvate kinase.

In the measurement method of the present invention, isolation of blood cells primarily means isolation of erythrocytes, and preferred examples thereof include a blood isolation method which is suitable for the above-described rapid measurement at bedside or in a clinic such as Point of Care Testing and measurement by patients themselves at home and uses a filtration material for isolating blood cells, which is particularly effective in the measurement of an extremely small amount of whole blood. The filtration materials for isolating blood cells are not particularly limited so long as they can isolate blood cells, and known filter materials can be used. Examples thereof include glass fiber filter papers, cellulose filter papers, microporous materials, polymer materials, and members that are combinations thereof.

The glass fiber filter paper preferably has a density of about 0.02 to 0.09, with the retained particle size being about 1 to 5 µm. The surface of the glass fiber may be treated with hydrophilic polymers, lectin as a sugar-binding protein, lecithin or phosphatidylcholine as an amphipathic lipid, and the like.

The cellulose filter paper is not particularly limited, and examples thereof include commonly used filter papers.

Examples of the microporous material include microporous membranes and microporous carriers, and those having a highly asymmetric structure can also be used. Examples of the microporous membrane include polysulfone membranes and fluorinated polymer membranes. Examples of the microporous carrier include gels and microspheres (e.g., beads and latex) having a nano/micro grain size, and examples of base materials thereof include polymers such as polystyrene, polymethacrylate, poly(hydroxymethacrylate), and polyvinyl alcohol, and silica. Microporous materials may be made hydrophilic by subjecting the surface to activity treatment such as oxygen plasma treatment.

Polymer materials are preferably hydrophilic polymer materials, and examples thereof include cellulose derivatives such as carboxymethylcellulose, polyvinylpyrrolidone, polyvinyl alcohol, gelatin, agarose, polyacrylic acid, polymers of maleic anhydride, polymethacrylic acid, polyacrylamide, polylysine, and polystyrenesulfonic acid. The above-mentioned glass fiber filter papers, cellulose filter papers, and microporous materials may be impregnated with the polymer material to make the surface hydrophilic, or the polymer material may be allowed to form a membrane themselves as with polyion complex membranes.

The above-mentioned filtration material for isolating blood cells may be used solely or as a member that is a combination thereof.

Furthermore, the above-mentioned filtration material for isolating blood cells may be filled in a lancet device or as a membrane-like member formed by applying on an electrode or the like used for the detection shown below directly or on an enzyme layer or the like on the electrode used for detection.

In the present invention, a substance converting glucose and/or a derivative thereof to a substance that does not interfere with measurement and whole blood may be brought into contact with each other by mixing these substances before blood cell isolation or allowing a blood cell isolation filter material to carry the substance converting glucose and/or a derivative thereof to a substance that does not interfere with measurement. Furthermore, the present invention encompasses a case where a part of the substance converting glucose and/or a derivative thereof to a substance that does not interfere with measurement is carried, and glucose and/or a derivative thereof is converted to a substance that does not interfere with measurement together with substances contained in an applied sample.

In the method for measuring a blood component of the present invention, methods for detecting a blood components are not particularly limited, and examples thereof include absorbance determination used in usual clinical chemistry examinations, electrochemical detection using an electrode or the like, and chemiluminescent and electrochemiluminescent techniques used in immunochemical tests.

The case where the blood component measured by the measurement method of the present invention is 1,5-anhydroglucitol will be further explained. Examples of the method for measuring 1,5-anhydroglucitol include known methods such as, for example, a method comprising allowing an enzyme having an ability of oxidizing 1,5-anhydroglucitol to act in the presence of an electron acceptor and measuring the amount of oxygen consumption, the reduced electron acceptor or reaction product after the reaction and a method comprising quantification by using 1,5-anhydroglucitol dehydrogenase, which catalyzes a direct reduction of a reducing coloring material in the absence of an electron acceptor. Furthermore, the measurement method may be a method comprising converting 1,5-anhydroglucitol to 1,5-anhydroglucitol-6-phosphate by 1,5-anhydroglucitol-6-phosphorylase, dehydrogenating 1,5-anhydroglucitol-6-phosphate by 1,5-anhydroglucitol-6-phosphate dehydrogenase in the presence of an oxidized coenzyme, and quantifying the generated component or deceased component in this reaction.

Examples of the enzyme having an ability of oxidizing 1,5-anhydroglucitol include enzymes classified according to the IUPAC-IUB nomenclature as pyranose oxidase (EC1.1.3.10) and L-sorbose oxidase (EC1.1.3.11). Specific examples thereof include pyranose oxidase produced by *Polyporus obtusus* ATCC26733 and L-sorbose oxidase produced by *Trametes sanguinea* IFO4923 which are described in JP-A-63-185397, oxidase produced by *Pseudomonas* sp. NK-85001 which is described in JP-A-62-79780, 1,5-anhydroglucitol dehydrogenase produced by fungi such as *Eupenicillium crustaceum* (IFO-8938) which is described in JP-A-2-268679, and 1,5-anhydroglucitol dehydrogenase produced by the *Agrobacterium tumefaciens* NT1130 strain described in Japanese Patent No. 2872983, which can dehydrogenate 1,5-anhydroglucitol without an electron acceptor.

Furthermore, as methods or enzymes used for converting 1,5-anhydroglucitol to 1,5-anhydroglucitol-6-phosphate, methods or reagents for phosphorylating glucose by the above-mentioned hexokinase or glucokinase to eliminate or convert glucose can be used as they are. Specific examples of the enzymes used include hexokinases, glucokinases, and ADP-dependent hexokinases. Examples of the ADP-dependent hexokinase include enzymes produced by the *Pyrococcus furiosus* DSM3638 strain which are described in JP-A-2002-186497. Preferred examples of the 1,5-anhydroglucitol-6-phosphate dehydrogenases include enzymes produced by *Escherichia coli* DH1 (ATCC33849) which are described in JP-A-10-191998.

Furthermore, an enzyme of a commercially available reagent for measuring 1,5-anhydro-D-glucitol (Lana 1,5-AG Auto Liquid: Nippon Kayaku Co., Ltd.) can be used.

Furthermore, detection methods for quantifying 1,5-anhydroglucitol are not particularly limited, and absorption photometry, electrochemical detection method, chemiluminescent techniques, electrochemiluminescent techniques, and the like can be used.

For example, for oxidized chromogenic substrates used for detection of absorbance, examples of solely used chromogens include N-carboxymethylaminocarbonyl-4,4'-bis(dimethylamino)diphenylamine sodium salt (DA64), 10-carboxymethylaminocarbonyl-3,7-bis(dimethylamino)phenothiazine sodium salt (DA67), bis[3-bis(4-chlorophenyl)-methyl-4-dimethylaminophenyl]amine (BCMA), bis[3-bis(4-chlorophenyl)-methyl-4-carboxyethylaminophenyl]amine, 10-N-methylcarbamoyl-3,7-dimethylamino-10H-phenothiazine (MCDP), 10-N-carboxymethylcarbamoyl-3,7-dimethylamino-10H-phenothiazine (CCAP), 3,3',5,5'-tetramethylbenzidine (TMBZ), and N,N,N',N',N'',N''-hexa(3-sulfopropyl)-4,4',4''-triaminotriphenylmethane hexasodium salt (TPM-PS). For coupling chromogens, examples of couplers include 4-aminoantipyrine (4AA), 3-methyl-2-benzothiazolinonehydrazone (MBTH), and aminodiphenyl compounds (NCP), and examples of Trinder reagents include N-ethyl-N-(3-methylphenyl)-N'-succinylethylenediamine (EMSE), N-ethyl-N-(2-hydroxy-3-sulfopropyl)-3-methoxyaniline (TOOS) and the like. Furthermore, for reduced chromogenic substrate, examples of chromogens include 2-(4-iodophenyl)-3-(4-nitrophenyl)-5-phenyl-2H-tetrazolium chloride (INT), 3-(4,5-dimethyl-2-thiazolyl)-2,5-diphenyl-2H-tetrazolium bromide (MTT), 3,3'-[3,3'-dimethoxy-(1,1'-biphenyl)-4,4'-diyl]-bis[2-(4-nitrophenyl)-5-phenyl-2H-tetrazolium chloride] (NTB), 2-(4-iodophenyl)-3-(4-nitrophenyl)-5-(2,4-disulfophenyl)-2H-tetrazolium monosodium salt (WST-1), and 2-(4-iodophenyl)-3-(2,4-dinitrophenyl)-5-(2,4-disulfophenyl)-2H-tetrazolium monosodium salt (WST-3).

Examples of the electrodes used for electrochemical detection include gold, platinum, carbon, palladium and silver. Examples of the measurement method include amperometry (electric current measurement method), coulometry (amount of electricity measurement method), potential sweep method, and cyclic voltammetry. Furthermore, naturally, mediators that mediate donation and acceptance of electrons may be used, and either oxidation mediators or reduction mediators may be used. Of these, oxidation mediators are more preferred, and known compounds can be used. Preferred examples thereof include ferricyanides, quinone compounds, osmium(III) complexes, and osmium (III) polymers thereof.

Furthermore, as the measurement method of the present invention, a method can also be used in which ADP-dependent hexokinase is allowed to act in the presence of ADP to convert glucose and 1,5-anhydroglucitol to glucose-6-phosphate and 1,5-anhydroglucitol-6-phosphate, respectively, phosphoglucoisomerase (a phosphohexose isomerase) and 6-phosphofructokinase are allowed to act to convert glucose-6-phosphate to fructose-1,6-bisphosphate, and 1,5-anhydroglucitol-6-phosphate dehydrogenase is allowed to act in the presence of coenzyme $NAD^+$ or $NADP^+$ to measure 1,5-anhydroglucitol-6-phosphate.

The present invention also includes a device having a blood cell isolation part and a detection part that can be used for the above-mentioned methods for measuring a blood component. The blood cell isolation part is used to perform the above-mentioned blood cell isolation, and the detection part is used to perform the above-mentioned detection of a blood component. The arrangement of these parts in the device may be vertical or horizontal, and these parts may be in or out of contact with each other. When these parts are out of contact, the shapes and positions thereof are not particularly limited so long as the parts can be brought into contact with each other at the time of detection. For example, when the whole surfaces of these parts are not in contact with each other, the blood cell isolation part and the detection part may be completely isolate or a part of one end or both ends may be in contact. The expression "can be brought into contact with each other at the time of detection" means that, after the application of a sample, the parts can be brought into contact with each other manually or automatically so that detection and quantification can be performed after time required for conversion of glucose and/or a derivative thereof to a substance that does not interfere with the measurement or blood cell isolation. In a convenient measurement, these parts are preferably brought into contact with each other at several seconds to several minutes after the application of a sample. Either the whole surface or a part thereof of the blood cell isolation part and the detection part are brought into contact with each other.

Furthermore, when the blood cell isolation part and the detection part are in contact with each other, whole blood and a substance converting glucose and/or a derivative thereof to a substance that does not interfere with the measurement may be brought into contact beforehand before blood cell isolation.

The detection part is not limited so long as it has a structure based on detection methods such as absorption photometry, electrochemical detection method using an electrode or the like, chemiluminescent methods, and electrochemiluminescent methods as described above.

As examples of the device of the present invention, simplified diagrams are shown in FIGS. 1 and 2.

The present invention also includes a 1,5-anhydroglucitol measurement kit that comprises the above-described device and a lancet device for blood collection.

The lancet device is not particularly limited so long as about several tens μL or less of whole blood can be collected, and may be the same as a lancet device attached to an apparatus for self-measurement of blood sugar levels.

EXAMPLES

The present invention will be explained more specifically with reference to the following examples. However, the scope of the present invention is not limited to these examples.

Example 1

1) Glucose Converting Reagent

In 25.0 mM 2-(4-(2-hydroxyethyl)-1-piperazinyl)ethane sulfonic acid (HEPES) buffer (pH 7.5), 7.38 mM $MgCl_2$, 49.6 mM KCl, 24.0 mM phosphoenolpyruvic acid (PEP), 1.0 mM ATP, 10 U/mL pyruvate kinase (PK), 8 U/mL glucokinase, 100 mM NaCl, 0.1 mM disodium ethylenedioxytetraacetate salt (EDTA.2Na), 0.1% $NaN_3$, 0.6 g/L bovine serum albumin (BSA), 0.05% nonionic surfactant HS210 (NOF Corporation), 0.1 mM potassium ferrocyanide, and 5 U/mL horseradish peroxidase (HRP) were dissolved in this composition, and the pH was adjusted to 7.5 to prepare a glucose converting reagent.

2) Coloring Reagent 8 mM NCP-04 (N-methyl-N-phenyl-p-phenylenediamine) and 8 mM TOOS were dissolved in 70% (v/w) ethanol in this composition to prepare a coloring reagent.

3) Enzyme Reagent

500 U/mL 1,5-anhydroglucitol oxidase and 500 U/mL HRP were dissolved in 1.0 M phosphate buffer in this composition, and the pH was adjusted to 7.5 to prepare an enzyme reagent.

4) Enzymatic Color Test Paper

Biodyne A membrane (PALL Corporation) 10 mm×45 mm was immersed in the coloring reagent obtained in the above 2) at room temperature for 10 minutes and dried at 50° C. for 20 minutes. Then, the membrane was immersed overnight in the enzyme reagent obtained in the above 3) and similarly dried at 50° C. for 20 minutes.

The membrane was cut into a 5 mm×5 mm piece to obtain an enzymatic color test paper.

5) Device

As shown in FIG. 1, a blood cell isolation part 3 (Hemasep L 5 mm×16 mm for blood cell isolation: PALL Corporation) was bonded on an adhesive surface of a support 4 (white PET 5 mm×50 mm) while aligning the left ends thereof. Meanwhile, the above-described enzymatic color test paper was bonded on the adhesive surface of a detection part support 2 (ARcare 8192 clear PET 5 mm×40 mm: Adhesives Research Inc.) as a detection part 1, while aligning the left end thereof. Finally, the detection part support 2 was bonded on the adhesive surface of the support 4 (white PET 5 mm×50 mm) so that the whole surface of detection part 1 and the right end of the blood cell isolation part 3 should overlap. Thus a device was prepared.

6) Creation of Calibration Curve

To create a calibration curve of 1,5-anhydroglucitol, 15 μL each of 3 whole blood specimens at known concentrations (the concentrations of 1,5-anhydroglucitol in the specimens obtained by the procedure in Reference Example 1 described later were 8.9, 18.5, and 28.5 μg/mL) and 15 μL of the glucose converting reagent were mixed in Eppendorf tubes and left stand for 5 minutes. Then, 15 μL each of the reaction mixtures was applied dropwise on the blood cell isolation part 3 at the position at which the specimen was applied in FIG. 1. When plasma after blood cell isolation reached the site of the blood cell isolation part 3 at which the detection part 1 (enzymatic color test paper) could be brought into contact, the detection part 1 was pressed, and absorbance was determined 60 seconds later by using a reflective photometer (colorimeter SUPER COLOR SP-80: Tokyo Denshoku Co., Ltd.). A calibration curve was created from the absorbances and the concentrations of 1,5-anhydroglucitol.

7) Measurement Procedure

15 μL each of whole blood from 6 normal subjects where 1,5-anhydroglucitol was to be measured was mixed with 15 μL of a glucose converting reagent in Eppendorf tubes and left stand for 5 minutes. Then, 15 μL each of the reaction mixture was applied dropwise on the blood cell isolation part 3 at the position at which the specimen was applied in FIG. 1. When plasma after blood cell isolation reached the site of the blood cell isolation part 3 at which the detection part 1 (enzymatic color test paper) could be brought into contact, the detection part 1 was pressed, and absorbance was determined 60 seconds later by using a reflective photometer. The amounts of 1,5-anhydroglucitol in the 6 whole blood specimens were obtained from the calibration curve. The results are shown in Table 1.

Reference Example 1

The same whole blood specimens from the 6 normal subjects used for the measurement in 7) of Example 1 were centrifuged at 3000 rpm for 5 minutes, and the supernatant was measured for 1,5-anhydroglucitol by a usual method using 1,5-anhydro-D-glucitol measurement reagent (Lana 1,5AG Auto Liquid: Nippon Kayaku Co., Ltd.) and Automated Analyzer 7150 (Hitachi, Ltd.) with the following parameters. The results are shown in Table 1.

| Analytical method | 2 point ends |
|---|---|
| Reading point | 24-50 |
| Volume of specimen | 8 μL |
| Lana 1,5AG Auto Liquid Pretreatment reagent (R1) | 240 μL |
| Lana 1,5AG Auto Liquid Color regent (R2) | 120 μL |
| Temperature | 37° C. |
| Measurement wavelength | (sub/main) 700/546 nm |

TABLE 1

| 1,5-ANHYDROGLUCITOL CONCENTRATION (μg/mL) | | |
|---|---|---|
| | Reference Example 1 | Example 1 |
| WHOLE BLOOD SPECIMEN 1 | 15.1 | 15.7 |
| WHOLE BLOOD SPECIMEN 2 | 19.9 | 20.2 |
| WHOLE BLOOD SPECIMEN 3 | 25.1 | 26.0 |
| WHOLE BLOOD SPECIMEN 4 | 15.4 | 14.7 |
| WHOLE BLOOD SPECIMEN 5 | 21.3 | 20.4 |
| WHOLE BLOOD SPECIMEN 6 | 17.5 | 17.3 |

The measured values of 1,5-anhydroglucitol in whole blood specimens on which the glucose converting reagent was allowed to act to convert glucose to a substance that does not interfere with measurement, from which blood cells were isolated, and which were further brought into contact with a detection reagent were consistent well with those obtained by a known measurement method in Reference Example 1, suggesting that 1,5-anhydroglucitol can be measured by the present invention.

Example 2

1) Glucose Converting Reagent

In 10.0 mM 2-morpholinoethanesulfonic acid (MES) buffer, 17.6 mM $MgCl_2$, 17.6 mM KCl, 175.7 mM phosphoenolpyruvic acid (PEP), 17.6 mM ATP, 123 U/mL pyruvate kinase (PK), 97 U/mL hexokinase, and 20 U/mL ascorbic acid oxidase were dissolved in this composition, and the pH was adjusted to 7.0 to obtain a glucose converting reagent.

2) Electrode Reagent 16 mg/mL osmium(III) complex ([Os(III) $(bipyridyl)_2$ $(imidazoyl)_2Cl]Cl_2$) and 465.2 U/mL 1,5-anhydroglucitol oxidase were dissolved in purified water in this composition to prepare an electrode reagent.

3) Sensor Chip

A detection part 1 of a carbon electrode was coated with 4 μL of the electrode reagent obtained in the above 2) and dried at 50° C. for 13 minutes to prepare a sensor chip.

4) Device

As shown in FIG. 2, a blood cell isolation part 3 (Hemasep L 5 mm×15 mm for blood cell isolation: PALL Corporation) was bonded on the detection part 1 of the sensor chip so that the farthest end should be covered. Thus, a device was prepared.

5) Creation of Calibration Curve

To create a calibration curve of 1,5-anhydroglucitol, 20 μL each of 3 whole blood specimens at known concentrations (the 1,5-anhydroglucitol concentrations in the specimens obtained by the above-described procedure in Reference Example 1 were 9.4, 18.6, and 42.6 μg/mL) and 10 μL of the glucose converting reagent were mixed in Eppendorf tubes and left stand for 5 minutes. Then, 20 μL each of the reaction mixtures was applied dropwise on the blood cell isolation part 3 at the potion at which the specimen was applied in FIG. 2. At 80 seconds after, plasma after blood cell isolation reached a detection part 1 (electrode reagent), a voltage was applied at 0.15 V for 10 seconds. Currents were measured 5 seconds later using an electrochemical detector (8-channel multipotentiostat with GPIB RS232C, MODEL PS-08: Toho Giken). A calibration curve was created from the current values and the concentrations of 1,5-anhydroglucitol.

6) Measurement Procedure

20 μL each of whole blood from 4 normal subjects for which 1,5-anhydroglucitol was to be measured and 10 μL of glucose converting reagent were mixed in Eppendorf tubes and left stand for 5 minutes. Then, 20 μL each of the reaction mixtures was applied dropwise on the blood cell isolation part 3 at the position at which the specimen was applied in FIG. 2. At 80 seconds after, plasma after blood cell isolation reached the detection part 1 (electrode reagent), a voltage was applied at 0.15 V for 10 seconds. Currents were measured 5 seconds later using an electrochemical detector. The amounts of 1,5-anhydroglucitol in 4 whole blood specimens were obtained from the calibration curve. The results are shown in Table 2.

Reference Example 2

The same whole blood specimens as measured in Example 2 of 6) were measured for 1,5-anhydroglucitol by the same manner as in Reference Example 1. The results are shown in Table 2.

TABLE 2

| 1,5-ANHYDROGLUCITOL CONCENTRATION (μg/mL) | | |
|---|---|---|
| | Reference Example 2 | Example 2 |
| WHOLE BLOOD SPECIMEN 7 | 17.5 | 18.2 |
| WHOLE BLOOD SPECIMEN 8 | 24.4 | 24.5 |
| WHOLE BLOOD SPECIMEN 9 | 28.2 | 26.8 |
| WHOLE BLOOD SPECIMEN 10 | 31.5 | 32.5 |

The measured values of 1,5-anhydroglucitol in whole blood specimens on which the glucose converting reagent was allowed to act on to convert glucose to a substance that does not interfere with measurement, from which blood cells were isolated, and which were further reacted with the electrode reagent were consistent well with those obtained by a known measurement in Reference Example 2, suggesting that 1,5-anhydroglucitol can be measured by the present invention.

DESCRIPTION OF SYMBOLS

Figure 1:
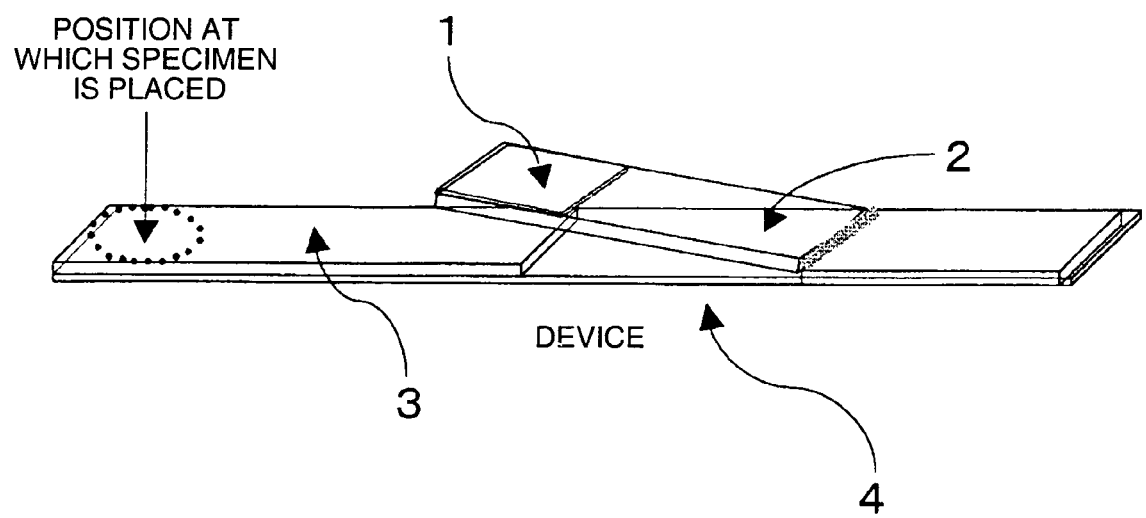
FIG. 1 is a simplified diagram showing a device used in Example 1.
Figure 2:
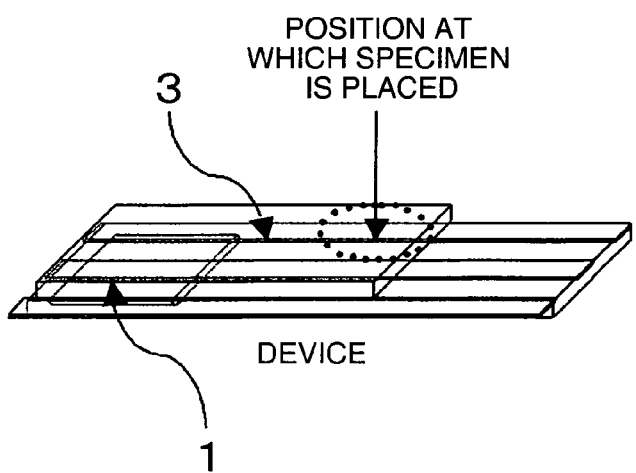
FIG. 2 is a simplified diagram showing a device used in Example 2.

1 Detection part
2 Detection part support
3 Blood cell isolation part
4 Support

The invention claimed is:
1. A method for measuring 1,5-anhydroglucitol that is subject to interference caused by glucose and/or a derivative thereof, which comprises the steps of:
bringing a whole blood sample collected from a subject directly into contact with a substance converting glucose and/or a derivative thereof to a substance that does not interfere with the measurement of 1,5-anhydroglucitol, wherein the substance converting glucose and/or a derivative thereof to a substance that does not interfere with the measurement of 1,5-anhydroglucitol is a substance for enzymatic oxidation or enzymatic phosphorylation of glucose;

thereafter isolating blood cells from the whole blood sample by using a filtration material for blood cell separation; and thereafter measuring 1,5-anhydroglucitol in the sample.

2. The method according to claim 1, wherein the amount of whole blood is not more than 20 μL.

3. The method according to claim 1, wherein the filtration material for blood cell separation is a glass fiber filter paper, a cellulose filter paper, a microporous material, a polymer material, or a member that is a combination thereof.

4. The method according to claim 1, wherein the converting substance contains one or more compounds selected from the compound group consisting of phosphoenolpyruvic acid, α-ketoglutaric acid, oxaloacetic acid, acetylphosphoric acid, pyruvic acid, 3-phosphoglyceric acid, creatine phosphate, adenosine-5'-diphosphate, adenosine-5'-triphosphate, oxidized or reduced nicotinamide adenine dinucleotide, and oxidized or reduced nicotinamide adenine dinucleotide phosphoric acid.

5. The method of claim 1, wherein said measurement of said 1,5-anhydroglucitol is performed by absorbance, electrochemical detection, chemiluminescence or electrochemical luminescence.

* * * * *